United States Patent [19]

Qinxiu et al.

[11] Patent Number: 5,304,722
[45] Date of Patent: Apr. 19, 1994

[54] HYBRID RICE PRODUCTION UTILIZING PERENNIAL MALE STERILE RICE PLANTS

[75] Inventors: Li Qinxiu; Alfonso G. Calub, both of East Bernard, Tex.

[73] Assignee: Ring Around Products, Inc., Prattville, Ala.

[21] Appl. No.: 906,664

[22] Filed: Jun. 30, 1992

Related U.S. Application Data

[62] Division of Ser. No. 550,952, Jul. 11, 1990, Pat. No. 5,158,879.

[51] Int. Cl.$^5$ .......................... A01H 5/00; A01H 1/00
[52] U.S. Cl. .................................... 800/200; 800/250; 800/DIG. 57; 47/58; 435/172.2
[58] Field of Search ....... 800/200, 205, 250, DIG. 57; 47/58.03, 58.05; 435/172.2

[56] References Cited

U.S. PATENT DOCUMENTS

| | | | |
|---|---|---|---|
| 3,842,538 | 10/1974 | Barabas | 47/58 |
| 4,305,225 | 12/1981 | Yuan | 47/58 |
| 4,351,130 | 9/1982 | Rutger et al. | 47/58 |
| 4,764,643 | 8/1988 | Calub | 800/1 |
| 4,999,945 | 3/1991 | Calub | 47/58 |

OTHER PUBLICATIONS

Yabuno (1987) Euphytica 36(2):529–534 Biological Abstract #84:94221.

"Hybrid Rice–Problems and Potentials", by J. W. Stansel and J. P. Craigmiles, Rice Journal, vol. 69, No. 5, pp. 14 to 15, and 46 (1966).

"Outlook for Hybrid Rice in the USA", by H. L. Carnahan, J. R. Erikson, S. T. Tseng, and J. N. Rutger, Rice Breeding, International Rice Research Institute, Laguna, Phillipines, pp. 603 to 607 (1972).

"Outlook for Hybrid Rice in India", by M. S. Swaminathan, E. A. Siddig, and S. D. Sharma, Rice Breeding, International Rice Research Institute, Laguna Phillipines, pp. 609 to 613 (1972).

"Current Status and Future Prospects for Breeding Hybrid Rice and Wheat", S. S. Virmani and Jan B. Edwards, *Advances in Agronomy*, vol. 36, pp. 145 to 214 (1983).

"A Concise Course in Hybrid Rice", by Long P. Yuan, Hunan Science and Technology Publishers, Hunan, China, pp. 1 to 168 (1985).

"Current Status of Hybrid Rice Research and Development", by L. P. Yuan and S. S. Virmani, International Symposium on Hybrid Rice, Changsha, Hunan, China, pp. 1 to 16 plus tables (1986).

"Standardization of parameters for seed production techniques in hybrid rice", by V. N. Sahoe et al, *Seed & Farms*, 11(7), pp. 9 to 14 (Jul. 1985).

"A Note on the Improved Method of Vegetative Seed Propagation in Hybrid Rice", by M. Jaganathan et al., *Seed Research*, vol. 10(2): 209–212 (1982).

*Primary Examiner*—Gary Benzion
*Attorney, Agent, or Firm*—Burns, Doane, Swecker & Mathis

[57] ABSTRACT

An improved process for the economical production of $F_1$ hybrid *Oryza sativa* plants (i.e., hybrid rice plants of the first filial generation) is provided. Novel female fertile male sterile rice plants which are perennial and capable of retaining viability through the winter are planted in combination with annual female fertile male fertile restorer plants which are killed during the winter. Accordingly, the substantial expense of establishing the required male sterile plants at the beginning of each growing season effectively is eliminated. The seeds formed on the perennial male sterile plants are capable of forming annual male fertile $F_1$ hybrid *Oryza sativa* plants. In preferred embodiments additional properties are incorporated into the parent rice plants (as described) which further enhance the $F_1$ seed production.

11 Claims, 5 Drawing Sheets

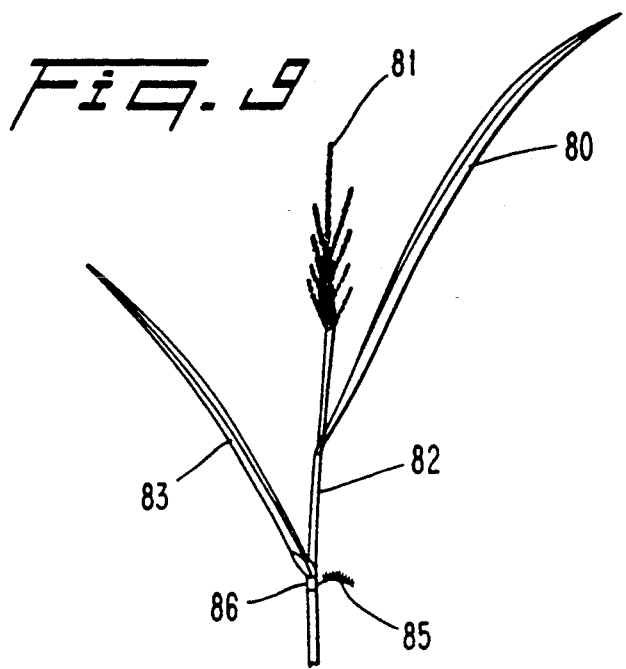
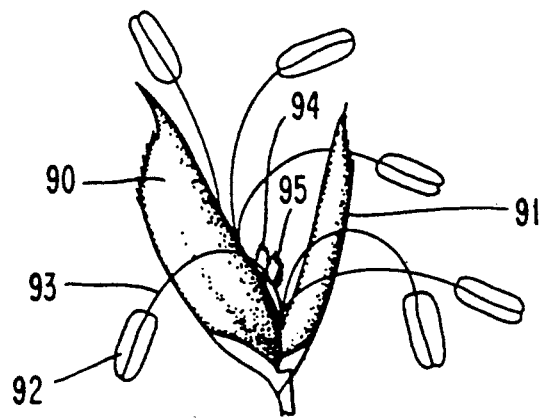

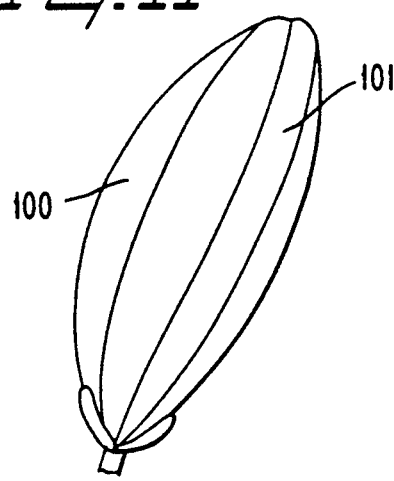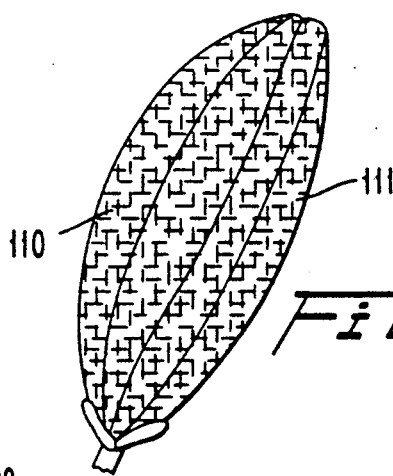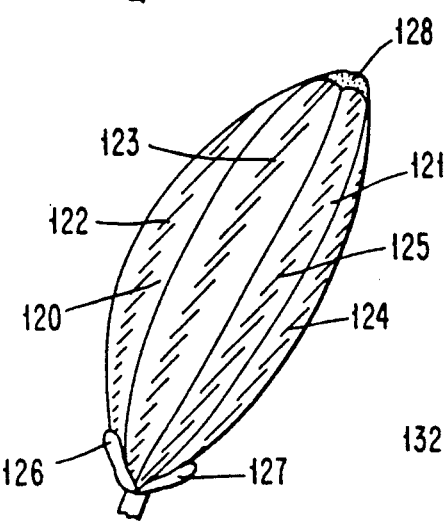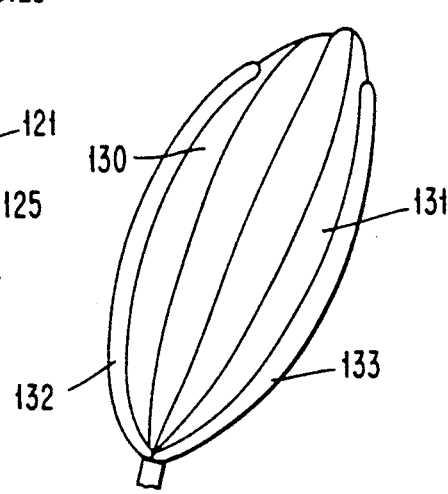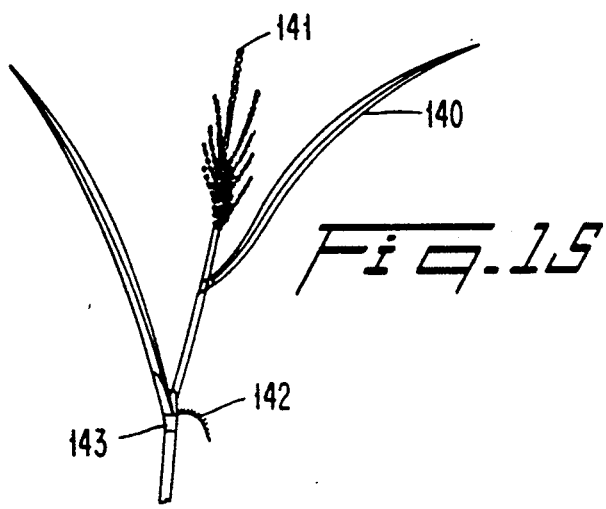

HYBRID RICE PRODUCTION UTILIZING PERENNIAL MALE STERILE RICE PLANTS

This application is a continuation of application Ser. No. 07/550,952, filed Jul. 11, 1990 now U.S. Pat. No. 5,158,879.

BACKGROUND OF THE INVENTION

Rice (i.e. *Oryza sativa*) is recognized to be an important food crop in many parts of the world. However, heretofore rice production has not benefited to a substantial degree from heterosis or hybrid vigor made possible when different parental lines are cross-pollinated. For a number of reasons primarily related to the unique rice plant morphology, the controlled cross-pollination of rice plants has been difficult to achieve on a commercial scale.

Representative articles which discuss hybrid rice production are:

(1) "Hybrid Rice—Problems and Potentials", by J. W. Stansel and J. P. Craigmiles, Rice Journal, Vol. 69, No. 5, Pages 14 to 15, and 46 (1966).

(2) "Outlook for Hybrid Rice in the USA", by H. L. Carnahan, J. R. Erikson, S. T. Tseng, and J. N. Rutger, Rice Breeding, International Rice Research Institute, Laguna, Philippines, Pages 603 to 607 (1972).

(3) "Outlook for Hybrid Rice in India", by M. S. Swaminathan, E. A. Siddig, and S. D. Sharma, Rice Breeding, International Rice Research Institute, Laguna, Philippines, page 609 to 613 (1972).

(4) "Current Status and Future Prospects for Breeding Hybrid Rice and Wheat", S. S. Virmani and Jan B. Edwards, *Advances in Agronomy*, Vol. 36, Pages 145 to 214 (1983).

(5) "A Concise Course in Hybrid Rice", by Long P. Yuan, Hunan Science and Technology Publishers, Hunan, China, Pages 1 to 168 (1985).

(6) "Current Status of Hybrid Rice Research and Development", by L. P. Yuan and S. S. Virmani, International Symposium on Hybrid Rice, Changsha, Hunan, China, Pages 1 to 16 plus tables (1986).

In Long P. Yuan U.S. Pat. No. 4,305,225, techniques are disclosed for aiding the production of hybrid rice. For instance, the male sterile seed parent plants can be sprayed with a growth hormone (e.g., gibberellin) in order to cause the flower-bearing panicles to more fully emerge from the rice leaf sheath. Any portion of the panicle which does not emerge will be incapable of receiving pollen from the pollen parent and thereby diminishes the yield of seeds capable of forming $F_1$ hybrid rice. The application of the growth hormone adds a significant expense to the overall process.

In J. Neil Rutger et al U.S. Pat. No. 4,351,130 a rice hybridization process is disclosed wherein the male pollinator plants are recessively inherited tall plants.

In Zoltan Barabas U.S. Pat. No. 3,842,538 is disclosed a hybrid seed production process wherein hybrid grains and pure grains are separated on the basis of color. Unlike wheat and similar grains, rice grains possess an outer hull which if removed will normally reduce their viability for planting purposes.

Heretofore, rice production has been carried out in the Peoples Republic of China using a highly labor intensive technique wherein the male and female rice parents are first seeded separately at different times in different beds, transplanted to different adjoining areas, monitored for growth on a weekly basis by observing the leaf count, the rate of growth is adjusted by water and fertilizer management, a growth hormone such as gibberellin is applied to the seed parent plants in order to cause the flower panicles to be more fully exserted out of the leaf sheath, the flag leaves of the seed parent plants are clipped, if wind currents are deficient pollen sometimes is transferred by hand through the movement of a rope across the planting area, and the seeds which are capable of forming $F_1$ hybrid rice plants are selectively harvested.

In Alfonso G. Calub U.S. Pat. No. 4,764,643 is disclosed an improved economically feasible procedure for forming *Oryza sativa* plants wherein the requisite parent plants possess a novel combination of certain specified properties. Such process requires the use of three different plant lines, i.e., (1) cytoplasmically male sterile rice plants, (2) maintainer plants to make possible the increase of the cytoplasmically male sterile plants, and (3) restorer plants to impart male fertility to the resulting $F_1$ *Oryza sativa* plants. The use of the maintainer plants and the annual planting of the two parent plants adds to the overall cost of the hybrid rice product. The present invention represents an improvement over such technology.

Also, during the last five years Chinese scientists have developed an additional approach to hybrid rice production which is commonly called the "two-line system". In this system, photoperiod sensitive genetic male sterile rice plants are utilized with restorer rice plants. When less than approximately fourteen hours of daylight are experienced, the photoperiod sensitive rice plants behave as maintainer plants, and when the light is more than approximately fourteen hours per day, the photosensitive rice plants exhibit male sterility. Accordingly, in theory the photoperiod sensitive rice plants can form seeds via self-pollination in the fall which can be planted to form male sterile rice plants in the spring. One thus avoids the necessity of increasing the male sterile plants by the tedious and time-consuming planting of the same in uniform populations adjacent maintainer plants coupled with the selective harvest of the seeds formed on the male sterile plants. However, it is understood that such technology at this stage relies not only on the length of daylight but also is significantly affected by variability in temperature which cannot be controlled. Hence, the reliability of the two-line system is still highly questionable.

It is an object of the present invention to provide an improved process for forming seeds capable of forming male fertile $F_1$ *Oryza sativa* plants on an ongoing basis which is capable of being readily implemented on a commercial scale.

It is an object of the present invention to provide an improved process for forming seeds capable of producing male fertile $F_1$ hybrid *Oryza sativa* plants on an ongoing basis which eliminates the annual expense of increasing the seeds required to plant the male sterile rice parent plants.

It is an object of the present invention to provide an improved process for forming seeds capable of producing male fertile $F_1$ hybrid *Oryza sativa* plants on an ongoing basis wherein the provision of the required male sterile parent plants is handled in a highly efficient manner.

It is an object of the present invention to provide an improved process for forming seeds capable of producing male fertile $F_1$ hybrid *Oryza sativa* plants on an ongoing basis wherein the planting of male sterile parent plants is not required at the beginning of every growing season.

It is an object of the present invention to provide an improved process for forming seeds capable of producing male fertile $F_1$ hybrid *Oryza sativa* plants on an ongoing basis wherein there is a significantly reduced labor requirement.

It is a further object of the present invention to provide an improved process for forming $F_1$ *Oryza sativa* plants on an ongoing basis which can be carried out on a reliable and economically attractive basis with a significant reduction in production costs.

It is a further object of the present invention to provide novel improved *Oryza sativa* seed products which are useful in the establishment of the male sterile parent plants which are used in $F_1$ hybrid seed production.

It is another object of the present invention to provide novel improved male sterile *Oryza sativa* plants which are useful in $F_1$ hybrid seed production.

These and other objects as well as the scope, nature and utilization of the claimed invention will be apparent to those skilled in the art from the following detailed description and appended claims.

SUMMARY OF THE INVENTION

It has been found that an improved process for the production of seeds capable of growing annual male fertile $F_1$ hybrid *Oryza sativa* plants on an ongoing basis comprises:

(a) growing in a planting area a population of (i) perennial female fertile male sterile rice plants, and a population of (ii) annual female fertile male fertile rice plants which are capable of restoring male fertility to plants in the next following generation resulting from the pollination of population (i) by population (ii), (b) pollinating the population (i) with pollen derived from the population (ii) whereby seeds are formed on the plants of population (i) which are capable of forming annual male fertile $F_1$ hybrid *Oryza sativa* plants and seeds are formed on the plants of population (ii) as the result of self-pollination, (c) harvesting the seeds which have formed on the plants of populations (i) and (ii), (d) retaining the plants of population (i) through the following winter in the substantial absence of irrigation while exposed to ambient conditions with the retention of substantial viability and killing the plants of population (ii) while exposed to such conditions, (e) planting in the planting area during the next subsequent growing season an additional population of (ii) annual female fertile male fertile rice plants which are capable of restoring male fertility to plants resulting from the pollination of the surviving plants of population (i) by the additional population (ii), (f) pollinating the plants of the surviving population (i) with pollen derived from the plants of the additional population (ii) whereby seeds are formed on the plants of the surviving population (i) which are capable of forming annual male fertile $F_1$ hybrid *Oryza sativa* plants, and (g) harvesting the seeds which have formed on the surviving population (i) and the additional population (ii).

An *Oryza sativa* seed product is provided which consists of a substantially homogeneous assemblage of seeds which upon growth yield perennial female fertile cytoplasmically male sterile rice plants having substantially fully exserted stigmas, flag leaves which in the absence of cutting generally extend upwardly to a lesser maximum height than the tips of the panicles whereby the disposition of the flag leaves below the tips of the panicles is attributable to recessive genes, and the ability to form seeds which are associated with a dominantly inherited genetic marker.

A binary *Oryza sativa* seed product is provided which consists of seeds which upon growth yield (1) perennial female fertile genetically male sterile rice plants having substantially fully exserted stigmas, flag leaves which in the absence of cutting generally extend upwardly to a lesser maximum height than the tips of the panicles whereby the disposition of the flag leaves below the tips of the panicles is attributable to recessive genes, and the ability to form seeds which are associated with a dominantly inherited genetic marker, and (2) perennial maintainer plants for the (1) plants.

Plants of *Oryza sativa* are provided which exhibit a perennial growth habit, male sterility, substantially fully exserted stigmas, flag leaves which in the absence of cutting generally extend upwardly to a lesser maximum height than the tips of the panicles whereby the disposition of the flag leaves below the tips of the panicles is attributable to recessive genes, and the ability to form seeds which are associated with a dominantly inherited genetic marker.

BRIEF DESCRIPTION OF THE DRAWINGS

FIG. 9 shows a portion of a representative annual female fertile male fertile restorer rice plant which is suitable for use in a preferred embodiment of the process of the present invention. The flag leaf 80 at the time of flowering is long and erect and extends upwardly to a greater maximum height than the tip of the floral panicle 81. The configuration of the flag leaf 80 at the time of flowering is attributable to dominant genes. The floral panicle 81 is substantially fully exserted from the leaf sheath 82 in the absence of the application of a growth hormone; however, it is not essential that the floral panicle be substantially fully exserted as illustrated. The configuration of leaf 83 below the flag leaf 80 also is erect; however, it optionally may assume a different configuration. In this preferred embodiment a vegetative marker in the form of substantially purple-colored auricle 85 and a substantially purple-colored collar 86 also is present.

FIG. 10 shows an enlarged schematic presentation of a representative open floret from the floral panicle of a preferred annual female fertile male fertile restorer rice plant of FIG. 9 which is particularly suited for use in the process of the present invention. The lemma 90 and palea 91 open to an angle of approximately 30 to 45 degrees; however, the angle of opening optionally may be lesser. A representative stamen is composed of an anther 92 and a filament 93. The anthers preferably are extruded so that they remain outside even when the lemma 90 and palea 91 are permanently returned to their unopened position. The anthers will disperse viable pollen which preferably has a relatively long fertility duration. The disposition of stigmas 94 and 95 is not important to the operation of the process of the present invention.

FIG. 11 shows an enlarged schematic presentation of a preferred rice grain with hull capable of growing the annual male fertile $F_1$ hybrid rice plants which may be formed in accordance with the process of the present invention. The hull consisting of the lemma 100 and palea 101 is straw-colored as the result of a dominantly inherited trait.

FIG. 12 shows an enlarged schematic presentation of a preferred rice grain with hull which may result from the self-pollination of the annual female fertile male fertile restorer rice plant during the course of the process of the present invention. The hull consisting of lemma 110 and palea 111 is gold-colored as the result of a recessively inherited trait. The gold-colored hull of FIG. 12 can readily be separated from the straw-colored hull of FIG. 11 through the use of mechanical seed-sorting equipment.

FIG. 13 shows an enlarged schematic presentation of a preferred rice grain with hull which may be formed in accordance with the process of the present invention. The hull consisting of lemma 120 and palea 121 possesses distinctive dark-brown longitudinal furrows 122, 123, 124 and 125, rudimentary glumes 126 and 127, and a purple-colored apiculus 128. Each of these Characteristics is dominantly inherited and can be present individually or in combinations of two or more. Such characteristics alone or in combination can be used as a basis for seed separation in the process of the present invention.

FIG. 14 shows an enlarged schematic presentation of a preferred rice grain with hull which may result from the self-pollination of an annual female fertile male fertile restorer rice plant during the course of the process of the present invention. The hull consisting of lemma 130 and palea 131 is relatively smooth and lacks dark-brown longitudinal furrows. Large empty glumes 132 and 133 are present, and a purple-colored apiculus is absent. Each of these characteristics is recessively inherited and can be encountered individually or in combinations of two or more. Such characteristics alone or in combination can be used as a basis for seed separation in the process of the present invention.

FIG. 15 shows a representative portion of an annual male fertile $F_1$ hybrid rice plant resulting from seed formed in accordance with the process of the present invention. Unlike the seed parent plants of FIGS. 3, 4, 5, 6 and 7, the flag leaf 140 at the time of flowering extends upwardly to a greater maximum height than the tip of the panicle 141 whereby efficient photosynthesis can be accomplished. It will be noted, however, that the flag leaf 140 of the $F_1$ hybrid rice plant commonly will extend upwardly to a lesser extent than the flag leaf 80 of the annual female fertile male fertile restorer rice plant of FIG. 9 because the dominantly inherited trait for flag leaf disposition commonly is only partially expressed in the $F_1$ generation. In a preferred embodiment a vegetative marker in the form of a substantially purple-colored auricle 142 and a substantially purple-colored collar 143 is also present.

DETAILED DESCRIPTION OF PREFERRED EMBODIMENTS

Figure 1:
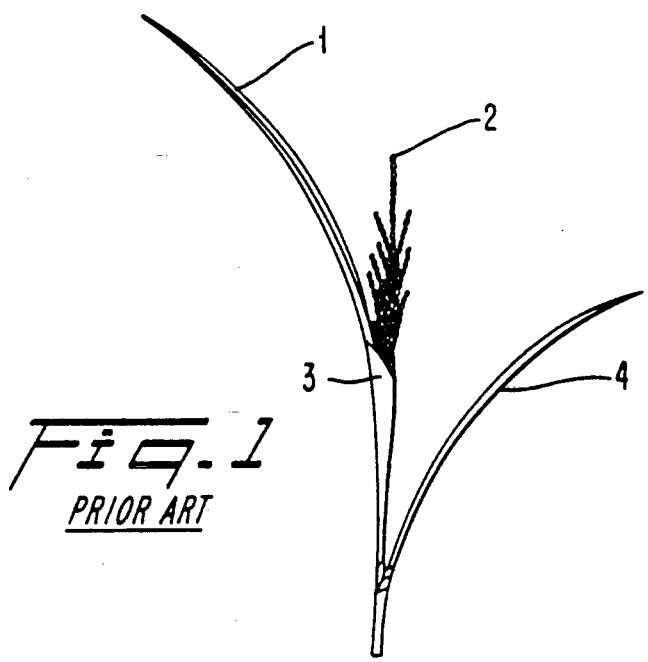
FIG. 1 shows a portion of a representative annual cytoplasmically male sterile rice plant of the indica type commonly encountered in the prior art wherein the flag leaf 1 at the time of flowering in the absence of cutting extends upwardly to a greater maximum height than the tip of floral panicle 2, and approximately 10 to 25 percent or more of the panicle is non-exserted and is enclosed by leaf sheath 3. The leaf 4 below the flag leaf 1 is also erect.

Heretofore Oryza sativa whether of the indica or japonica types has been recognized to be an annual crop which dies during the winter and must be replanted at the beginning of each growing season. On the contrary the novel female fertile male sterile Oryza sativa plants required for use in accordance with the concept of the present invention are perennial in character and are capable of surviving the ambient winter conditions experienced at the planting area when present in the substantial absence of irrigation. Such perennial Oryza sativa plants can be of either the indica or japonica types and possess the ability to reliably and stably form live culms with undeveloped buds which remain dormant during the winter without loss of viability. Accordingly, in the spring the buds grow and develop into new rice plants similar to those formed when seeds capable of forming annula Oryza sativa plants are planted annually. The new growth commonly originates from the culm and disk in the spring. Such perennial plants commonly can be relied upon to refoliate and flower each spring for seven years or more, and preferably ten years or more (e.g., for approximately 10 to 15 years or more) following the initial planting as described hereafter. Commonly, perennial female fertile male sterile *Oryza sativa* plants of the present invention can withstand average temperatures during the coldest winter month of at least as low as 9° C., and preferably at least as low as 5° C. It will be understood that *Oryza sativa* plants of the japonica type commonly can withstand even lower temperatures than those of the indica type.

It has been found that the perennial trait required for use in the present invention is controlled by a series of quantitative dominant genes which must be present in a sufficient concentration of more than three genes if the perennial phenotype is to be expressed. As the dominant genes for the perennial trait are diluted, the annula trait is displayed as it heretofore has been consistently displayed in *Oryza sativa* plants.

Empirical research has established that the perennial quantitative genes for the requisite perennial trait can be derived from certain wild rices such as those grown in West Africa which commonly have the ability to survive extended periods of time when dormant during a dry season. Suitable progenitors for the perennial trait are *Oryza longistaminata* and *Oryza rufipogon* with the latter being particularly preferred source. Such quantitative genes can be transferred to *Oryza sativa* through a controlled breeding program, involving the use of at least one bridge cross designed to bring about the needed interspecific transfer, or by using other available transfer techniques which are known to those skilled in plant technology. Such techniques include tissue culture (somaclonal, cell, anther), genetic engineering, protoplast fusion, embryo rescue, etc.

The key perennial female fertile male sterile *Oryza sativa* plants for use in accordance with the concept of present invention possess male sterility which is either cytoplasmic or genetic in character. Such cytoplasmic male sterility owes its origin to cytoplasmic-genetic factors and is well known to those familiar with prior techniques for hybrid rice production. On the contrary the genetic male sterility owes its origin solely to nuclear genes and is also well known to those familiar with prior techniques from hybrid rice production.

Preferred cytoplasms for the perennial cytoplasmically male sterile *Oryza sativa* plants of the present invention may be derived from a sporophytic system using an annula indica source, such as WA (wild abortive), Gam (Gambiaca), DW (dwarf wild rice with aborted pollen), ARC (IRRI line), L (lead rice), *Oryza glaberrima* (OG), dwarf abortive (DA), Birco (BC), *Oryza nivara* (OV), etc., or from a gametophytic system from a japonica source, such as BT (Chinsurah Borro II), Teichung I (TN1), *Oryza rufipogon* (rfp), etc. Other cytoplasmically male sterile cytoplasms alternatively may be selected. Suitable sources for such publicly available annula cytoplasmically male sterile *Oryza sativa* plants include: L301A, 97A, Lemont A, D297A, Zhen Shan 97A, II32A, Xiu Lin A, 08A, 09A, PMS1, PMS2, PMS3, PMS4, PMS5, PMS6, PMS7, PMS8, PMS9, PMS10, Liu Qian Xin A, Dang Xuan Wan 2A, IR45752A, IR46826A, IR46 430A, Shi Jin A, etc.

Preferred genetically male sterile plants of the present invention may be derived from available annula genetically male sterile *Oryza sativa* plants. These plants possess a pair of recessive msms genes for male sterility. Specific publicly available annula *Oryza sativa* plants which possess genetic male sterility are IR36ms, 3024A, 926A, etc. Such genetic sterility, as well as appropriate maintainer plants for the same, may be obtained from IRRI (Philippines) and the Crop Science Institute, Sichuan Academy of Agricultural Science, Chengdu, Sichuan (Peoples Republic of China), etc.

The restorer plants which are selected for use in the present invention are annual in nature and are incapable of withstanding the winter at the planting area when exposed to ambient conditions. Such restorer plants supply the pollen which pollinates the perennial female fertile male sterile rice plants and are capable of restoring fertility to the plants of this cross in the next following generation. If cytoplasmic male sterility is utilized such plants possess a normal cytoplasm (i.e., an N cytoplasm) and if genetic male sterility is utilized, such plants possess a pair of dominant MsMs genes which overcome the male sterility of the female parent. The resulting progeny are annual male fertile $F_1$ hybrid *Oryza sativa* plants which lack winter hardiness and are killed during the winter. Accordingly, such restorer plants also contribute genes which dilute the quantitative dominant genes for the perennial trait of the female parent to the requisite degree that the $F_1$ progeny no longer manifests the perennial trait. Accordingly, the rice grower is provided with seeds, which are capable of growing annual *Oryza sativa* plants with which he is well familiar.

The parent plants for use in the process of the present invention are selected so that at least a general synchronization of flowering occurs. Thereby, pollen from the restorer plants is present when the florets of the seed parent plants are receptive to pollination. Also, it is preferable that the parent plants possess relatively smooth leaf surfaces which are substantially incapable of retaining the pollen which contacts the same. Accordingly, the pollen released by the restorer plants has a greater potential to reach florets of the seed parent plants.

In a preferred embodiment at least one of the parent plants possesses the wide compatibility gene which will make possible a wider cross using more diverse parents. Suitable publicly available sources for the wide compatibility gene include P1868 from the Peoples Republic of China; CP-SL017 and CP-SL019 from India; Narin, BPI-176, N22, Moroberekan, Dular, PBMN1, Palawan, and Fussa from IRRI; and Calotoc, Ketan Nangba, and Nekken 1 from Japan; etc. Accordingly, it is preferred that one of the parents be of the indica type and the other of the japonica type thereby resulting in increased heterosis.

Figure 17:
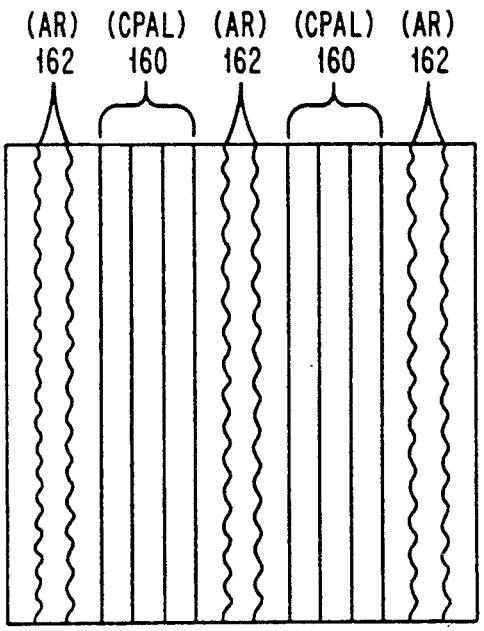
FIG. 17 shows a preferred planting pattern whereby seeds capable for forming annual male fertile $F_1$ hybrid Oryza sativa plants are formed in accordance with the concept of the present invention. Fours rows of perennial female fertile cytoplasmically male sterile Oryza sativa plants 160 (designated CPAL) alternate with two rows of annual male fertile restorer plants for the same 162 (designated AR). Pollen from plants 162 pollinates plants 160 and the resulting seeds capable of forming annual male fertile $F_1$ hybrid Oryza sativa plants are selectively harvested from plants 160. During the next subsequent growing season plants 162 are replanted and the process steps are repeated. As discussed hereafter, other planting patterns and ratios may be utilized.

In accordance with the process of the present invention the required perennial female fertile male sterile plants and annual female fertile male fertile *Oryza sativa* plants are simultaneously grown in pollinating proximity to each other in a planting area as either a substantially random population or as substantially uniform populations of each parent. The plants commonly are planted in rows using conventional *Oryza sativa* planting procedures. In a preferred embodiment the plants are planted in rows with approximately 6 to 7 inches between plants and approximately 7 to 8 inches between rows. Also, when the parent plants are planted as substantially uniform populations these preferably assume the configuration of alternating blocks consisting of more than one row of each parent with the perennial female fertile male sterile plants being present in greater numbers. For instance, four to ten rows of the seed parent (as described) may alternate with two to five rows of the male restorer parent (as described). See, the representative preferred planting patterns of FIGS. 17 and 19 where four rows of seed parents (as described) alternate with two rows of male restorer parents (as described). Alternatively, when the parent plants are grown in a substantially random population, commonly approximately 70 to 95 percent of the plants in the planting area are the perennial female fertile male sterile plants, and approximately 5 to 30 percent of the plants in the planting area are the restorer plants. When the parent plants are grown in a substantially random population, the proportion of perennial female fertile male sterile plants can be maximized if desired.

During the course of the process of the present invention the perennial female fertile male sterile rice plants are pollinated with pollen from the annual female fertile male fertile restorer plants and the restorer plants are self-pollinated. The pollen transfer between the restorer plants and the perennial male sterile plants commonly is carried out by wind transport. However, other means capable of moving the pollen alternatively can be selected.

The seeds which have formed on the perennial male sterile plants and the restorer plants next are harvested at an appropriate time in their maturity. Such harvesting can be efficiently carried out through the use of a conventional rice combine. When the parent plants are grown as substantially uniform populations the seeds formed on the same may be selectively harvested from each parent. Alternatively, the seeds formed on both parent plants can be harvested in bulk. If the seeds are harvested in bulk, they optionally may be subsequently separated on the basis of a genetic marker as described hereafter. Following harvest the planting area is drained.

During the following winter the restorer plants are killed by the action of the cold ambient temperatures encountered and perennial female fertile male sterile plants survive while remaining in a dormant state. It is essential that the planting area be maintained in the substantial absence of irrigation during the winter so as to promote dormancy in the absence of deleterious conditions which could promote rotting.

At the appropriate time during the next subsequent growing season an additional population of annual female fertile male fertile Oryza sativa restorer plants is planted in the planting area which is capable of restoring male fertility to the $F_1$ hybrid plants resulting from the pollination of the surviving perennial female fertile male sterile rice plants. The planting pattern used during the next subsequent growing season is influenced by that originally selected during the preceding season. For instance, if the restorer plants were originally planted as a substantially uniform population, substantially the same planting pattern is used during the next subsequent growing season. If the restorer plants were originally present in a substantially random population, such planting pattern preferably is repeated during the next subsequent growing season. For best results when a random planting pattern is utilized, the entire planting area is cultivated in a shallow manner of no more than approximately 10 to 15 cm. prior to the reemergence of the dormant perennial female fertile male sterile rice plants. Such cultivation may be carried out with a tooth harrow; the disc or coulter blade portion of a no till and drill planter such as that manufactured by The Tye Company of Lockney, Tex. 79241, U.S.A.; John Deere & Co.; Case International Harvester; Massey-Ferguson, Inc., etc. Such light cultivation has been found to further promote new growth at the base of the culm and disk of the perennial female fertile male sterile parent plants.

The resulting parent plants undergo pollination in the next subsequent growing season with the newly planted restorer plants supplying pollen to the perennial female fertile male sterile rice plants, and the restorer plants undergoing self-pollination. The resulting seeds are harvested as heretofore described. Such process steps can be again repeated for at least one additional growing season (e.g., 1 to 10 or more additional growing seasons) without the need to ever replant and reestablish the perennial female parent plants. This results in a savings of considerable costs.

In accordance with preferred embodiments of the claimed invention the perennial seed parent plants and restorer Oryza sativa plants utilized in the present invention are further modified (as described) such as described in U.S. Pat. No. 4,764,643 in order to incorporate additional properties which improve various aspects of the hybridization and provide the possibility for efficient seed separation.

Annual indica cytoplasmically male sterile Oryza sativa rice plants heretofore available commonly have possessed the undesirable trait as illustrated in FIG. 1 of having a portion of the floral panicle inserted within the leaf sheath. The japonica Oryza sativa cytoplasmically male sterile rice plants do not possess this undesirable trait. Accordingly, the florets present upon the inserted portion of the panicle of the indica rice plants are never provided access to the pollen required to achieve cross-pollination and the yield of seed capable of forming $F_1$ hybrid rice plants accordingly is diminished. In order to deal with this deficiency a growth hormone such as gibberellin sometimes has been applied in the prior art to cause increased peduncle growth and the full exsertion of the floral panicle.

In preferred embodiments of the present invention perennial female fertile male sterile rice plants which optionally may possess cytoplasmic male sterility are provided (e.g., as illustrated in FIGS. 3, 4, 5, 6, and 7) which possess panicles which at the time of flowering are substantially fully exserted from the leaf sheath most preferably in the absence of the application of a growth hormone in combination with the other essential characteristics recited herein. Accordingly, the florets along the full length of the panicles have access to pollen. The achievement of such substantially full panicle exsertion in the cytoplasmically male sterile plants of the indica type can be produced by the introduction of such trait from an appropriate source such as pureline selections from the crosses Belle Patna/Zenith//Belle Patna/-MOR 500, Saturn, Zenith, AS2004, the euieui germplasm (elongated upper internode-genetic tall recessive line 80-14549 available from J. Neil Rutger of Davis, Calif.), IR50eui (IRRI), and Zhen Shen 97-eui A (Peoples Republic of China); etc.

Figure 2:
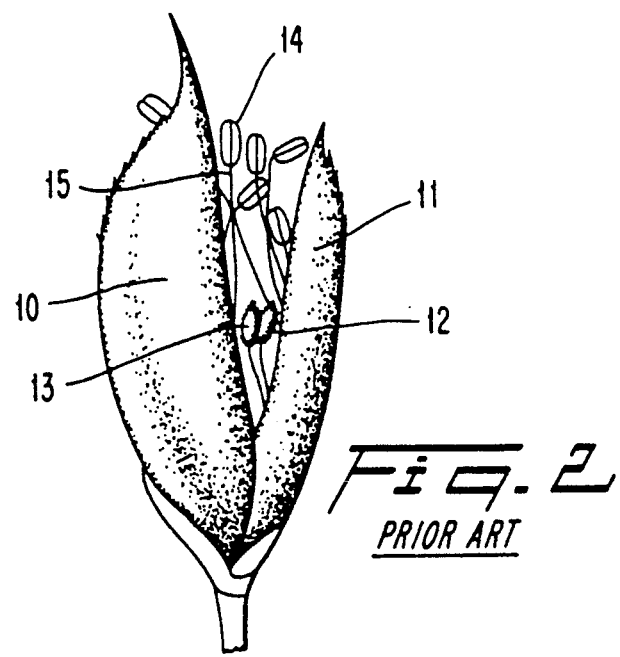
FIG. 2 shows an enlarged schematic representation of a representative open floret from the floral panicle of the annual cytoplasmically male sterile rice plant commonly encountered in the prior art as shown in FIG. 1. The lemma 10 and palea 11 open only once to a maximum angle of only approximately 10 to 25 degrees, and the pair of stigmas 12 and 13 borne on relatively short styles are non-exserted and are enclosed when the lemma 10 and palea 11 are permanently returned to their unopened positions. A representative stamen is composed of an anther 14 and a filament 15. No viable pollen is produced.

Also annual cytoplasmically male sterile rice plants heretofore reported have tended to display the usual rice stigma disposition as illustrated in FIG. 2. More specifically, the stigmas have tended to be situated well within the glume (i.e., the lemma and palea) of a given floret and to be available for receipt of pollen only for a relatively brief period of time (e.g., approximately 30 to 120 minutes) when the floret is open. Also, as illustrated in FIG. 2, during flowering the lemma and palea of the floret commonly open to an angle of only approximately 10 to 25 degrees.

Figure 8:
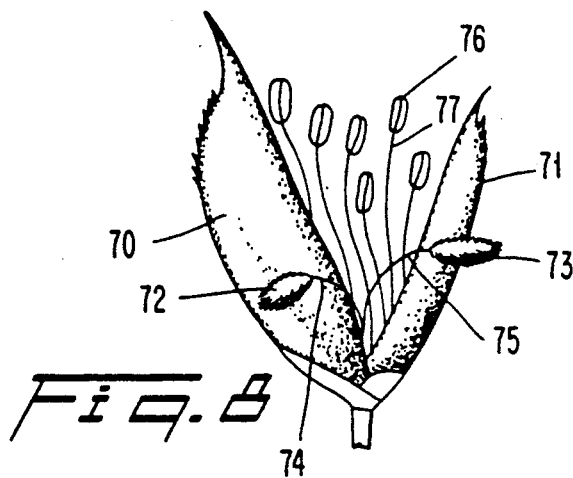
FIG. 8 shows an enlarged schematic presentation of a representative open floret from the floral panicle of the perennial cytoplasmically or genetically male sterile rice plants of FIGS. 3, 4, 5, 6 and 7 of the present invention. The lemma 70 and palea 71 open to a maximum angle of approximately 45 degrees; however, the angle of opening optionally may be lesser so long as the stigmas 72 and 73 which are borne on relatively long styles 74 and 75 are substantially fully exserted and remain substantially exposed even when the lemma 70 and palea 71 are permanently returned to their unopened position. The exact number of stigmas per floret may vary. A representative stamen is composed of an anther 76 and a filament 77. No viable pollen is produced.
Figure 16:
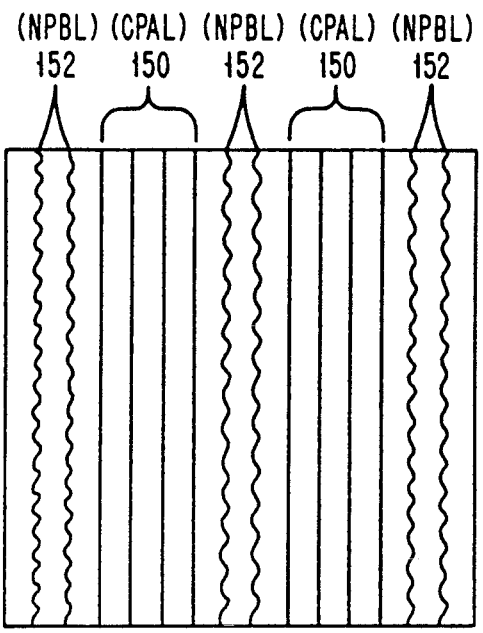
FIG. 16 shows a preferred planting pattern whereby seeds capable of forming perennial female fertile cytoplasmically male sterile Oryza sativa plants of the present invention can be formed in increased quantities. Four rows of perennial female fertile cytoplasmically male sterile rice plants 150 (designated CPAL) alternate with two rows of perennial male fertile maintainer plants for the same 152 (designated NPBL). Pollen from plants 152 pollinates plants 150 and seeds formed on plants 150 are selectively harvested and are available for future planting when carrying out the presently claimed process. As discussed hereafter, other planting patterns and ratios may be utilized.

In accordance with a preferred embodiment of the present invention perennial female fertile male sterile rice plants which optionally may possess cytoplasmic male sterility are provided (e.g., as illustrated in FIG. 8) which possess stigmas at the time of flowering which are substantially fully exserted. Such stigmas remain substantially exposed even after the lemma and palea close thereby substantially extending the period of time from up to 2 hours to approximately 4 to 5 days during which pollination can occur. Such stigma exsertion can be attributable to the length of the styles on which the stigmas are borne and/or the stigma length. Also, in a preferred embodiment as illustrated in FIG. 8 the lemma and palea open to a greater angle than normally encountered in rice florets which further aids in the disposition of the stigmas outside the lemma and the palea. In a particularly preferred embodiment the lemma and palea open to an angle of approximately 30 to 45 degrees. Also, in a preferred embodiment perennial female fertile male sterile rice plants optionally may be selected which possess more than the usual number of two stigmas per floret and accordingly exhibit three to five stigmas, or more per floret. The achievement of such substantially full stigma exsertion in the perennial female fertile male sterile plants can be produced by crossing an exserted stigma source such as *Oryza rufipogon* and/or *Oryza longistaminata* to *Oryza sativa*, making selections for 5 or 6 generations, crossing to a variety with good agronomic characteristics, making selections for 5 or 6 generations, crossing to a perennial female fertile male sterile line, making 5 or 6 backcrosses, and making a selection for perennial female fertile male sterile plants having the desired substantially fully exserted stigmas. In the past such exserted stigma characteristic generally has not been reported in *Oryza sativa* plants of the japonica type. Multipistillate rice plants can be derived from japonica cultivar wx 154 available from Yeungan University of Gyeongsa, Korea and the Sichuan Academy of Agricultural Science of the Peoples Republic of China; or a selection of Ratna×Rajai from CRRI of Cuttack, India; etc.

Heretofore, most male sterile rice plants utilized in hybrid rice production if left unaltered (as illustrated in FIG. 1) commonly have possessed a flag leaf which extends upwardly to greater maximum height than the tip of the floral panicle. Such flag leaf configuration is genetically controlled and as discussed in U.S. Pat. No. 4,764,643 has proven to pose a partial barrier to the receipt of pollen required for cross-pollination. In a rice hybridization process previously practiced in the Peoples Republic of China the upper portions of such flag leaves commonly are laboriously removed by cutting so as to remove this impediment to cross-pollination. Such cutting is highly time consuming, very expensive, and difficult to achieve with accuracy in the absence of concomitant damage to the floral panicles. The perennial female fertile male sterile rice plants preferably are modified so as to incorporate atypical flag leaves which at the time of flowering in the absence of cutting generally extend upwardly to a lesser maximum height than the tips of the panicles. Such lower disposition of the flag leaves is attributable to recessive genes (i.e., to a single pair of recessive genes). The disposition of the leaves below the flag leaf may optionally be independent of the flag leaf disposition and may be separately controlled. Also, in a preferred embodiment at least 50 percent of the total panicle height at the time of flowering generally extends above the maximum height of the flag leaves of the perennial female fertile male sterile rice plants. A high level of cross-pollination is made possible in the absence of any substantial obstruction posed by the flag leaves.

Figure 3:
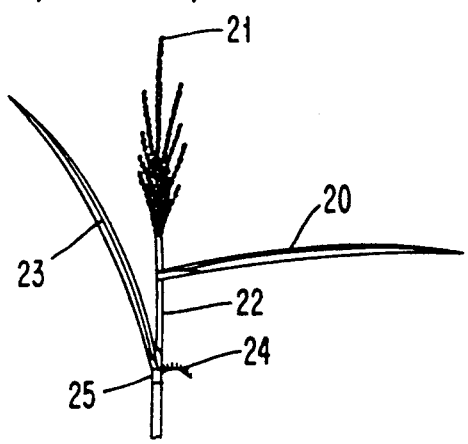
FIG. 3 shows a portion of a representative perennial cytoplasmically or genetically male sterile rice plant suitable for use in a preferred embodiment of the present invention wherein the flag leaf 20 at the time of flowering is disposed in a substantially horizontal configuration which is attributable to recessive genes. The flag leaf 20 at the time of flowering extends upwardly to a lesser maximum height than the tip of the floral panicle 21. Also, the panicle 21 is substantially fully exserted from the leaf sheath 22 in the absence of the application of a growth hormone. The leaf 23 below flag leaf 20 is erect; however, it optionally may assume a different configuration. In a preferred embodiment a vegetative marker in the form of a substantially white auricle 24 and a substantially white collar 25 also is present.

In a preferred embodiment of the present invention, the perennial female fertile male sterile rice plants at the time of flowering possess flag leaves which are disposed in a substantially horizontal configuration as illustrated in FIG. 3 which is attributable to recessive genes. The mature flag leaf in such embodiment commonly extends from the rice stalk at an angle of approximately 85° to 95° measured between the rice stalk and the lower surface of the flag leaf at the point of attachment. The substantially horizontal flag leaf character can be introduced into the male sterile seed parent plants by crossing with Bonnet Bell, pureline selections from Labelle/Melrose, CI9363, CI9373, CI9386, CI9406, CI9408, CI9414, etc.

Figure 4:
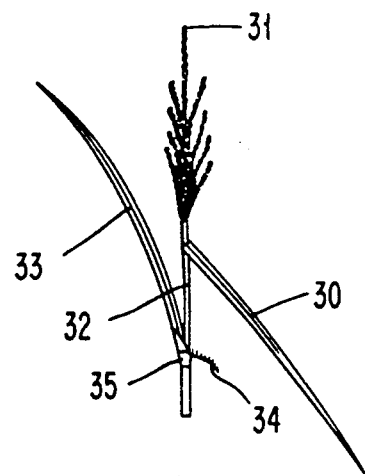
FIG. 4 shows a portion of another representative perennial cytoplasmically or genetically male sterile rice plant suitable for use in a preferred embodiment of the present invention wherein the flag leaf 30 at the time of flowering is disposed in a decumbent configuration which is attributable to recessive genes. The flag leaf 30 at the time of flowering extends upwardly to a lesser maximum height than the tip of the floral panicle 31. Also, the panicle 31 is substantially fully exserted from the leaf sheath 32 in the absence of the application of a growth hormone. The leaf 33 below the flag leaf 30 is erect; however, it optionally may assume a different configuration. In a preferred embodiment a vegetative marker in the form of a substantially white auricle 34 and a substantially white collar 35 also is present.

In another preferred embodiment of the present invention the perennial female fertile male sterile rice plants at the time of flowering possess flag leaves which are disposed in a decumbent configuration (i.e., are generally borne at an angle with respect to the rice stalk of no more than approximately 80 degrees) as illustrated in FIG. 4 which is attributable to recessive genes. Commonly such decumbent flag leaves are borne at an angle of approximately 40 to 80 degrees with respect to the rice stalk. The decumbent flag leaf character can be introduced into the perennial female fertile male sterile seed parent plants by crossing with Labelle, selections from CI9157/G630, CI1658, CI8993, PI229266, etc.

Figure 5:
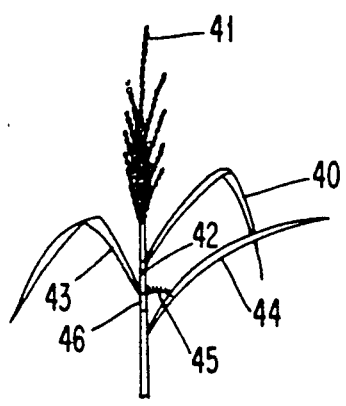
FIG. 5 shows a portion of another representative perennial cytoplasmically or genetically male sterile rice plant suitable for use in a preferred embodiment of the present invention wherein the flag leaf 40 at the time of flowering is disposed in a downwardly arching configuration which is attributable to recessive genes. The flag leaf 40 at the time of flowering extends upwardly to a lesser maximum height than the tip of the floral panicle 41. Also, the panicle 41 is substantially fully exserted from the leaf sheath 42 in the absence of the application of a growth hormone. The configurations of leaves 43 and 44 below the flag leaf 40 may be varied. In a preferred embodiment a vegetative marker in the form of a substantially white auricle 45 and a substantially white collar 46 also is present.

In another preferred embodiment of the present invention, the perennial female fertile male sterile rice plants at the time of flowering possess flag leaves which are disposed in a downwardly arching configuration as illustrated in FIG. 5 which is attributable to recessive genes. The downwardly arching flag leaf character can be introduced into the perennial female fertile male sterile seed parent plants by crossing with Lebonnet, Brazos, CI12091, CI2971, CI3336, CI4285, CI4286 etc.

Figure 6:
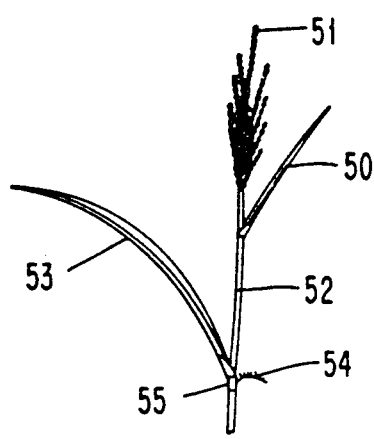
FIG. 6 shows a portion of another representative perennial cytoplasmically or genetically male sterile rice plant suitable for use in a preferred embodiment of the present invention wherein the flag leaf 50 at the time of flowering is short and substantially erect with such configuration being attributable to recessive genes. The flag leaf 50 at the time of flowering extends upwardly to a lesser maximum height than the tip of the panicle 51. Also, the floral panicle 51 is substantially fully exserted from the leaf sheath 52 in the absence of the application of a growth hormone. The configuration of leaf 53 below flag leaf 50 is erect; however, it optionally may assume a different configuration. In a preferred embodiment, a vegetative marker in the form of a substantially white auricle 54 and a substantially white collar 55 also is present.

In another preferred embodiment of the present invention, the perennial female fertile male sterile rice plants at the time of flowering possess flag leaves which are disposed in a short substantially erect configuration as illustrated in FIG. 6 which is attributable to recessive genes. In such embodiment the mature flag leaf is short in the sense that it does not extend as high as the tip of the panicle in spite of its erect and generally upright disposition. The short erect flag leaf character can be introduced into the perennial female fertile male sterile seed parent plants by crossing with Brachytic Nato, selections from Brachytic Nato/C57, PI321216, PI321318, PI373832, CI19002, etc.

Figure 7:
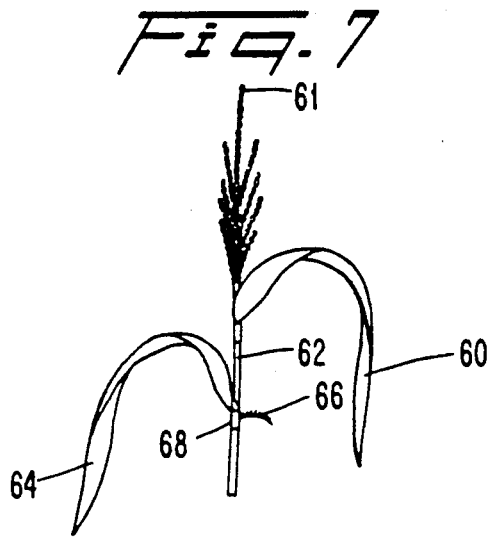
FIG. 7 shows a portion of another representative perennial cytoplasmically or genetically male sterile rice plant suitable for use in a preferred embodiment of the present invention wherein the flag leaf 60 at the time of flowering exhibits a reverse drooping configuration which is attributable to dd recessive genes. The flag leaf 60 at the time of flowering droops downwardly significantly below the tip of the panicle 61. The dd genes lead to the absence of the usual leaf midstem which significantly influences the drooping configuration. Such drooping is considered to be "reverse" in the sense that the flag leaf inherently assumes a twisted configuration with the upper leaf surface facing somewhat downwards at the end of the leaf rather than upwards. Also, such plants tend to exhibit a round stem from the three-leaf stage to the point of panicle initiation while common rice varieties tend to exhibit a somewhat flattened stem at such area. The floral panicle 61 is substantially fully exserted from the leaf sheath 62 in the absence of the application of a growth hormone. The configuration of leaf 64 below flag leaf 60 also exhibits a reverse drooping configuration; however, it optionally may assume a different configuration. In a preferred embodiment a vegetative marker in the form of a substantially white auricle 66 and a substantially white collar 68 also is present.

In another particularly preferred embodiment of the present invention, the perennial female fertile male sterile rice plants at the time of flowering possess flag leaves which are disposed in a reverse drooping configuration as illustrated in FIG. 7 which is attributable to the dd recessive genes. The reverse drooping flag leaf character can be introduced into the perennial female fertile male sterile seed parent by crossing with RGS20 which is publicly available from IRRI (Philippines). The reverse drooping flag leaf character is particularly suited for use with perennial female fertile male sterile rice plants which possess genetic male sterility since such trait has been found capable of being closely linked with such male sterility and is further useful as a marker during the initial establishment of such male sterile plants as discussed hereafter.

Finally, it is preferred that the perennial female fertile male sterile plants of the present invention possess the ability to form seeds which are associated with a dominantly inherited genetic marker. Such marker is either on or about the rice hull. As described hereafter, such genetic marker will enable the separation of seeds capable of growing male fertile $F_1$ hybrid rice plants formed thereon from seeds formed on the male parent restorer plants as the result of self-pollination. Markers on the rice seeds per se are ineffective for use in the present invention since the rice seeds are located within a protective hull. If such hull is removed to expose the seed, the capability of the rice seed to produce a rice plant is greatly reduced.

In a preferred embodiment such dominantly transmitted genetic marker which is associated with the seeds is a straw-colored hull as illustrated in FIG. 11. The straw-colored hull characteristic is common in rice plants and can be introduced into the male sterile seed parent plants by crossing with Labelle, Lebonnet, Newrex, Della, Starbonnet, Bonnet 73, Lemont, Bellemont, Nato, Vista, Saturn, Brazos, Nova 76, Mars, M201, S201, L301, Katy, Rexmont, etc.

In other embodiments the dominantly transmitted genetic marker which is associated with the seeds as illustrated in FIG. 13 consists of distinctive dark-brown longitudinal furrows 122, 123, 124, 125 on the lemma and palea 120 and 121, rudimentary glumes 126 and 127, a purple-colored apiculus 128, or combinations of two or more of these. The dark-brown longitudinal furrow characteristic can be introduced into the perennial female fertile male sterile seed parent plants by crossing with Ikam Podchee. The rudimentary glumes optionally can possess a distinctive coloration and can be introduced into the perennial male sterile seed parent plants by crossing with Nortai, PI408449, CI5309, purple Starbonnet, etc. The purple-colored apiculus can be introduced into the cytoplasmically male sterile seed parent plants by crossing with Nortai, Bonnet 73, PI408449, PI321158, PI321161, PI1321185, CI9864, CI9865, CI9866, etc.

Additional representative dominantly transmitted markers which optionally can be associated with the seeds of the perennial male sterile plants of the present invention include purple-colored hulls, white-colored hulls, rough/pubescent hull surfaces, and depressed palea. The rough/pubescent hull surfaces can be introduced into the perennial female fertile male sterile seed parent plants by crossing with Calrose 76, Earlirose, Colusa, Caloro, Yong Kwang, PI321213, PI321216, etc. The depressed palea can be introduced into the cytoplasmically male sterile seed parent plants by crossing with ECCA-90.

The perennial female fertile male sterile rice plants of the present invention also possess at least one additional marker which manifests itself in the vegetation so that the seed parent plants readily can be distinguished from the male fertile restorer plants. Such marker enables one readily to confirm the presence of the male sterile plants and further provides means to determine the approximate concentration of the same in a given rice plant population. Accordingly, such markers provide those who produce seeds capable of growing male fertile $F_1$ hybrid rice plants with a means to well monitor the required seed parent plants prior to and during utilization in the process of the present invention. Corrective action can be taken at an early stage in the hybrid seed production process should this be required. Unwanted plants can be rogued from the area if a certain marker or combination of markers is absent.

A preferred vegetative marker for use with the perennial female fertile male sterile plants of the present invention is a light (e.g., white, off-white, light-green, yellow, tan) auricle and collar. Such auricles are small hairy-like appendages which tend to be sickle-shaped situated adjacent the leaf collar at the junction of the leaf sheath and the leaf blade. The auricles and leaf collars are illustrated adjacent a single leaf in FIGS. 3, 4, 5, 6, and 7; however, in practice such auricles and collars commonly will recur a number of times in each rice plant in conjunction with each leaf. In a particularly preferred embodiment the light auricle and collar is substantially white as is common to most rice varieties. Alternatively, dark (e.g., purple, red, etc.) auricles and collars may be selected in less preferred embodiments. Such purple auricles and collars can be derived from Arborio, and selections from the cross of A8/-/VEC/G630. Recessively transmitted green leaf sheaths, green peduncles, and/or green leaf margins or dominantly transmitted purple leaf sheaths, purple peduncles, and/or purple leaf margins may be selected. Green leaf sheaths, green peduncles, and/or green leaf margins are common in many rice varieties. The purple leaf sheaths, peduncles, and margins may be derived from PI408449, CI5309, the cross of Labelle/Melrose//G630, purple Starbonnet, etc. Stigma color (e.g., dark stigmas such as purple or red stigmas vs. white stigmas) may be utilized as a vegetative marker. Purple stigmas can be derived from Nortai, V41A, V20A, Bonnet 73, CI5309, purple Starbonnet, PI408449, etc. Red stigmas can be derived from Lemont, Leah, etc. White stigmas can be derived from Phi-Gai, Newrex, IR24, R29, CI4285, CI9107, CI9297, etc. Also, the presence or absence of leaf pubescence can be used as a vegetative marker as can the presence or absence of reverse drooping leaves.

When carrying out the process of the present invention, annual female fertile male fertile rice plants are employed which are capable of restoring male fertility to the $F_1$ progeny of the perennial female fertile male sterile rice plants and possible other required characteristics recited herein including the ability to impart an annual character to the $F_1$ progeny. As illustrated in FIG. 9, such male parent restorer plants have generally long erect flag leaves attributable to dominant genes which generally extend upwardly to a greater maximum height than the tips of the panicles. Such male parents also may be derived from known rice varieties which have been modified by plant breeding or other means to incorporate the recessively inherited genetic marker associated with the seed as described hereafter. Representative commercially available rice varieties which exhibit dominantly inherited long erect flag leaves include Lemont, Bluebelle, Bonnet 73, Bellemont, IR24, IR36, IR54, G630, selections from the cross of IR24/Yuang Hsing, selections from the cross of LM/G630, Gulfmont, PI160832, PI321215, etc.

The restorer rice plants preferably possess the same genetic marker associated with the seeds as is present in the perennial female fertile male sterile seed parent rice plants with the exception that the marker is present in the homozygous recessive form in the restorer plants and is present in the homozygous dominant form in the seed parent plants. For instance, if the seed parent possesses a straw-colored hull as illustrated in FIG. 11, the restorer plants can possess a gold-colored hull as illustrated in FIG. 12. Such gold-colored hull can be introduced into the restorer plants by crossing a variety having a gold-colored hull with a restorer variety having a straw-colored hull, selecting plants having a gold-colored hull in the $F_2$ generation, backcrossing 4 to 6 times, and making the final selection. Rice plants having a gold-colored hull can be derived from Bluebelle, Dawn, gold Nato, Kar 398, Dular gold, Pecos, Kargat 184, CI9002, CI9003, CI9063, CI9122, CI9123, etc. If the seed parent possesses rudimentary glumes as illustrated in FIG. 13, the restorer plants can possess the long empty glumes as illustrated in FIG. 14 or rudimentary glumes of a different color. The presence of long empty glumes in the restorer plants can be derived from 83N1223 available from the Crowley Rice Experiment Station, Crowley, La., U.S.A. If the seed parent possesses a purple-colored apiculus, the restorer plants can possess a substantially white apiculus. Such white apiculus can be introduced into the restorer plants by crossing with Lebonnet, Bellemont, Newrex, Starbonnet, Brazos, Saturn, Mars, etc. If the seed parent possesses dark-brown longitudinal furrows on the hull, the restorer plants can possess a hull which lacks such dark-brown coloration, such as a straw-colored hull. Such absence of dark-brown hull coloration in the restorer plants is readily available in many rice varieties.

In a preferred embodiment the annual female fertile male fertile rice plants which serve as restorers also possess at least one additional marker which manifests itself in the vegetation so that the restorer plant readily can be distinguished from the perennial female fertile male sterile plants. In each instance the restorer rice plants possess the same vegetative marker or markers as present in the male sterile seed parent plants with the exception that such marker or markers are present in the reciprocal state (i.e., if present in the seed parent in a homozygous dominant form, are present in the restorer parent in the homozygous recessive form, or if present in the seed parent in a homozygous recessive form, are present in the restorer parent in the homozygous dominant form). For instance, in a preferred embodiment as illustrated in FIG. 9 the restorer plants will exhibit purple-colored auricles and purple-colored collars which are dominantly transmitted. An auricle and collar is illustrated adjacent a single leaf in FIG. 9; however, in practice the auricles and collars will recur a number of times in each rice plant in conjunction with each leaf.

As illustrated in FIG. 10, the annual female fertile male fertile restorer rice plants in a preferred embodiment additionally possess fully extruded anthers which are will able to disperse pollen. Such anthers are extruded in the sense that they protrude outside when the lemma and palea open. Such extruded anther characteristics can be introduced into the restorer plants by crossing with *Oryza longistaminata* and/or *Oryza rufipogon* followed by backcrossing and selection. It is preferred that the stigmas of the restorer plants be non-exserted so as to minimize the possibility of out-crossing. It also is preferred that the pollen be formed on the restorer plants over an extended period of time in abundant quantities and that it be light and buoyant to facilitate easy dispersion. Such pollen dispersion also is aided if the restorer plants are generally equal or greater in height than the seed parent plants. It is also preferred that the restorer plants produce pollen of relatively long fertility duration.

In those embodiments of the present invention in which no selective harvest of the seeds capable of forming annual male fertile $F_1$ hybrid *Oryza sativa* plants is carried out, the seeds capable of growing the $F_1$ hybrid rice plants formed on the perennial female fertile male sterile rice plants preferably are separated from the seeds formed on the restorer plants on the basis of a genetic marker which is associated with the seeds. Such separation preferably is carried out by mechanical separators. For instance, photoelectric seed-sorting equipment, velvet rolls, mechanical seed sorters which respond to seed size and/or shape such as Carter disks, etc., can be utilized. In a particularly preferred embodiment the seeds capable of forming $F_1$ hybrid rice plants possess a straw-colored hull and the seeds formed on the restorer plants possess a gold colored hull. The seeds having a gold-colored hull readily can be removed with ease at a high rate of speed using a photoelectric seed-sorting apparatus available from ESM International Inc., 10621 Harwin Drive, Suite 300, Houston, Tex. 77036, U.S.A. The seeds possessing the straw-colored hull can be sold to those wishing to obtain the additional yields made possible through hybrid vigor. The seeds bearing a gold-colored hull which were produced on the restorer plants can be sold for conventional rice usages or retained for planting as a restorer in another generation.

As illustrated in FIG. 15, a representative annual male fertile $F_1$ hybrid rice plant made possible by the process of the present invention unlike its perennial seed parent possesses a flag leaf which extends upwardly to a greater maximum height than the tip of the floral panicle. Accordingly, efficient photosynthesis is promoted in the $F_1$ generation in order to further maximize rice yields.

In a further preferred embodiment of the process of the present invention the purity of the desired seed product is monitored through a determination of whether the seeds initially used to form plants (i) of step (a) inadvertently had become contaminated with seeds which were formed on nearby maintainer plants during the formation of the planting seed used in step (a) to form plants (i). This conveniently can be done by providing the perennial seed parent plants (i) with recessively transmitted light (e.g., substantially white) auricles and collars, and providing the restorer plants (ii) with dark (e.g., substantially purple-colored) auricles and collars, growing at least a portion of the seeds (i.e., a representative sample) which are intended to form male fertile $F_1$ hybrid rice plants, and determining the approximate proportion of seeds capable of forming annual male fertile $F_1$ hybrid rice plants present therein having dark auricles and collars in comparison to undesired seeds which form plants having light auricles and collars resulting from the self-pollination of the maintainer plants. Accordingly, the seed formed in accordance with the process of the present invention for the formation of $F_1$ hybrid rice plants can be accurately labeled as to its purity.

Figure 18:
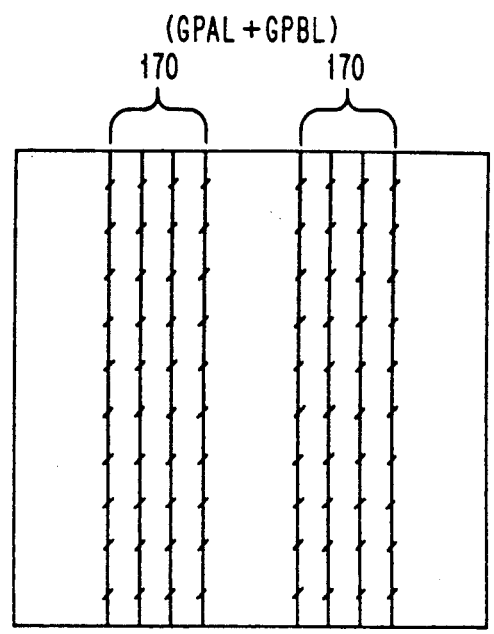
FIG. 18 shows a preferred planting pattern for the establishment of perennial female fertile genetically male sterile Oryza sativa plants which in the next subsequent growing season can be used to form $F_1$ hybrid plants in accordance with the present invention. Blocks of plants 170 (designated GPAL+GPBL) consisting of four rows each derived from a binary seed blend in accordance with the present invention are planted in a spaced relationship. Such plants constitute a mixture of perennial female fertile genetically male sterile Oryza sativa plants having an msms genotype (GPAL) and perennial maintainer plants for the same having a Msms genotype (GPBL). Following anthesis the maintainer plants (GPBL) can be cut or rogued from the field on the basis of one or more genetic markers (e.g., an erect flag leaf and a highly elongated internode spacing on GPBL vs. a reverse drooping flag leaf and a less elongated internode spacing on GPAL). One is then left with spaced substantially homogeneous populations of perennial female fertile genetically male sterile Oryza sativa plants (GPAL). The seeds which are harvested from the same may be used in the establishment of an additional planting area while using the same procedure. Alternatively, one may eliminate the perennial GPBL plants prior to anthesis in the same year the perennial female fertile genetically male sterile Oryza sativa plants are established and form the seeds capable of growing $F_1$ hybrid Oryza sativa plants in the first year of planting.
Figure 19:
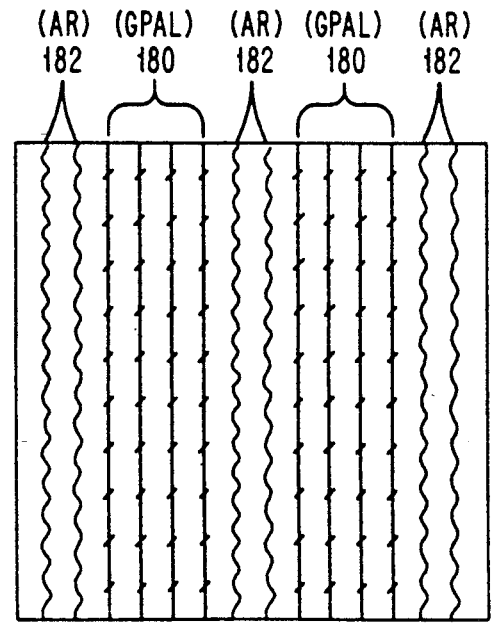
FIG. 19 shows a preferred planting pattern for the formation of seeds capable of growing annual male fertile $F_1$ hybrid Oryza sativa plants in accordance with the present invention while using the spaced substantially homogeneous populations of female fertile genetically male sterile Oryza sativa plants 180 produced as described in connection with FIG. 18. Two rows of male fertile restorer plants 182 (designated AR) are planted as alternating blocks in relation to the perennial male sterile plants 180. Pollen formed on plants 182 pollinates plants 180, and the seeds capable of growing annual male fertile $F_1$ hybrid Oryza sativa plants formed on plants 180 preferably are selectively harvested. As discussed hereafter, other planting patterns and ratios may be utilized.

As was previously discussed in conjunction with FIGS. 18 and 19, the initial establishment of the perennial female fertile genetically male sterile parent plants in the planting area requires an elimination step for non-conforming plants which are simultaneously produced since it generally is impossible to supply the required planting seed for such seed parent plants in a pure form. The necessity for such plant elimination can be traced to segregation which results in the progeny plants which include the required perennial female fertile genetically male sterile parent plants. The genetically male sterile seed parent plants possess a msms genotype and are formed by crossing seed parent plants having the same msms genotype and pollinator plants having the Msms genotype. Such cross simultaneously also produces fully fertile plants having the Msms genotype. Such plants possessing the Msms genotype must be substantially eliminated from the planting area prior to the anthesis used for $F_1$ hybrid *Oryza sativa* seed production. Appropriate marker genes may be incorporated into the msms and Msms plants so that they can be distinguished one from the other and the fully fertile plants possessing the Msms genotype eliminated by rouging or other means. In a preferred embodiment such markers are the reverse drooping flag leaf of FIG. 7 attributable to recessive genes dd linked to genetic male sterility and an elongated uppermost internode length attributable to recessive genes euieui vs. an erect flag leaf attributable to dominant genes DD and also the elongated uppermost internode length attributable to recessive genes euieui. It has been found that the reverse drooping flag leaf character tends to be tightly linked to the genetic male sterility trait. It has been found that the reverse drooping leaf character commonly starts to be apparent at the third leaf stage of the rice plant thereby facilitating the roguing or elimination of plants of the Msms maintainer line which lack this trait. It also has been found that although the euieui gene is present on both the genetically male sterile plants (msms) and the male fertile plants (Msms), its expression with respect to the degree of the uppermost internode length is different in each instance. More specifically, in the genetically male sterile plants (msms), the euieui gene causes the panicle to exsert so that it extends just outside of the sheath of the flag leaf. If the euieui gene were absent, approximately $\frac{1}{4}$ to $\frac{1}{3}$ of the panicle would be inserted within the leaf sheath. However, in male fertile plants (Msms), the euieui gene causes the panicle to exsert approximately 15 to 20 cm. or more beyond the sheath of the flag leaf. Accordingly, the total plant height of the male fertile plants (Msms) often is 20 to 40 cm. taller than the desired sterile plants (msms). Both traits (i.e., reverse drooping flag leaf and less than full expression of the euieui gene) can be used as a basis for plant preservation when hand roguing or other form of plant elimination is practiced. Since the male fertile plants (Msms) are taller, they can be conveniently spotted for hand roguing or can be killed following contact with a wick herbicide applicator which contacts only the taller plants. This procedure can be utilized to establish the genetically male sterile rice plants for the first year of $F_1$ rice production in accordance with the process of the present invention. Similarly, since the male fertile plants (Msms) are taller, they optionally can be effectively eliminated immediately following anthesis by mechanized cutters. Thereby one is able to increase the seed formed on the msms A line without undue dilution because of the presence of male fertile seeds formed on the maintainer plants.

The present invention provides a highly efficient improved route to the production of seeds capable of growing annual male fertile $F_1$ hybrid *Oryza sativa* plants on an ongoing basis wherein worthwhile heterosis is exhibited. The resulting $F_1$ *Oryza sativa* hybrids can result in increased rice production of approximately 10 to 40 percent or more depending upon the combining ability of the specific parent plants which are selected. As previously indicated, a greater heterosis tends to be exhibited when one of the parent plants is of the indica type and the other is of the japonica type.

The following Examples are presented as specific illustrations of the claimed invention. It should be understood, however, that the invention is not limited to the specific details set forth in the Examples.

EXAMPLE I

The Nigeria 31 variety of *Oryza glaberrima* served as a source of germplasm. This was an annual fully fertile cultivated wild rice variety which was introduced from West Africa into Sichuan, Peoples Republic of China, for growing prior to 1974. A cytoplasmically male sterile mutant was selected from within this variety and was crossed with pollen from an annual fully fertile *Oryza sativa* plant TY29 of the japonica type to produce annual cytoplasmically male sterile progeny. These progeny were backcrossed with the recurrent parent designated TY29 with selection being made for male sterility. This selection was backcrossed with TY29 and the $BC_2$ was designated Guang Keng A. The Guang Keng A plant which served as an appropriate bridge parent was then crossed with pollen from wild perennial fully fertile *Oryza rufipogon* to produce a plant designated Gl-1. Such perennial *Oryza rufipogon* parent lacked rhizomes and possessed a fully exserted stigma in combination with some undesirable traits such as tendency to shatter, photosensitivity, tallness, red grain kernels, long awns, reduced fertility, long leaves, and somewhat poor grain quality. The fertile Gl-1 progeny was next crossed with pollen from wild perennial *Oryza longistaminata* to produce a fully fertile perennial $F_1$ plant designated 4020-1. The *Oryza longistaminata* parent possessed a very long stigma and the same undesirable traits as *Oryza rufipogon*. The 4020-1 progeny exhibited cold resistance to $-8°$ C. and was handcrossed to an established maintainer line designated V20B to produce an $F_1$ plant which subsequently was selfed to the $F_4$ generation and a selection was made which was designated C205. Line C205 while used as a pollinator was further handcrossed to Line 2597B (i.e., an $F_3$ selection derived from 4020-1 $F_1$) to produce a perennial semi-dwarf plant designated 7B67 having a long stigma and large panicles. An $F_3$ selection of 7B67 was used as a female and was crossed with Line 29218 to produce an $F_1$ plant designated 4312. Line 29218 was an $F_4$ selection derived from RGS20×C205 which possessed the reverse drooping flag leaf trait attributable to dd genes. The $F_1$ designated 4312 was a perennial maintainer for cytoplasmic male sterility having a reverse drooping flag leaf as illustrated in FIG. 7. This 4312 plant was next crossed with an established maintainer for cytoplasmic male sterility designated D297B (which was capable of producing good quality rice grains and high yield) to produce a plant designated 421B. P1686, an annual Japonica variety which contained the wide compatability gene, was crossed with a plant designated 610A (an $F_2$ derivative of a Japonica cytoplasmically male sterile plant from $F_1$ 4020-1) to obtain a perennial Japonica breeding line designated 32114. This perennial 32114 plant was crossed with 421B to obtain an $F_1$ plant designated 9005-9. Plant 9005-9 while used as a pollinator was crossed to Line D297A having a WA cytoplasm and the $F_1$ was backcrossed to advanced recurrent parent 9005-9 to obtain a stable cytoplasmically male sterile 9005-9 line. As the recurrent backcross was made, 9005-9 was simultaneously selfed to an advanced generation for homozygosity. To date 9005-9B (Nmsms) is in the $F_6$ generation and the 9005-9A (Smsms male sterile with WA cytoplasm) is in the $BC_4$ generation. Both materials have been stabilized and both are perennial in character and produce reverse drooping leaves as illustrated in FIG. 7, fully exserted stigmas, translucent grains, high yield potential, cold resistance to 3° C., and other improved agronomic characteristics such as a non-shattering grains, absence of awns, absence of rhizomes, non-photosensitivity, short to medium plant heights, high fertility, good tillering, short leaves, fully exserted panicles, etc. Also, the rice grains possess straw-colored hulls which can serve as a dominantly inherited genetic marker.

Seeds capable of forming the perennial female fertile cytoplasmically male sterile *Oryza sativa* plants designated 9005-9A, and the perennial female fertile male fertile maintainer plants for the same designed 9005-9B, are to be deposited under the Budapest Treaty in the American Type Culture Collection, 12301 Parklawn Drive, Rockville, Md. 20852, U.S.A. under Accession Nos. 40918 and 40919 respectively. These seed deposits will be made available upon the maturation of this application into a patent. However, the availability of these seeds is not to be construed as a license to practice this invention in contravention of rights granted under the authority of any government in accordance with its patent or breeder's rights law.

Such 9005-9A plants can be used when carrying out the process of the present invention as described herein. Preferred publicly available restorers for use with such perennial female fertile cytoplasmically male sterile *Oryza sativa* plants are Min Hui 63, R29, and R594 from the Peoples Republic of China, and IR24 and IR26 from the Philippines. R594 possesses gold-colored hulls which can serve as a recessively inherited genetic marker. However, additional parent plants which satisfy the prerequisites set forth herein can be independently provided and utilized with equally advantageous results.

EXAMPLE II

The plant 4020-1 (discussed in connection with Example I) was crossed to the annual Kennong variety of *Oryza sativa*. The $F_1$ segregant line 6015-2 was selected based on the perennial trait and was crossed to IR24 of the indica type. The resulting $F_1$ plant was then crossed to both IR36ms and 926A and resulting $F_1$ plants from both crosses were advanced to the $F_4$ generation and selected lines from this generation of both crosses were further crossed with each other to produce $F_1$ plants which were advanced to the $F_9$ generation. In each generation the selection was based on indica type, the perennial trait as evidenced by cold tolerance to 5° C., the absence of rhizomes, nonshattering grain character, complete fertility, absence of awns, long stigma, white kernel grains, a non-photosensitive response, medium plant height, and short leaves. This $F_9$ selection was crossed to DY-1, a japonica variety possessing high cold tolerance and high yield potential to obtain a perennial $F_1$ plant designated 267. The resulting 267 plant was crossed to P1868, a japonica variety possessing the wide compatibility gene and high yield potential to obtain a perennial fertile plant designated 8267. The 8267 plant was crossed to a female fertile genetically male sterile plant designated d2 derived from RGS20×297B having the reverse drooping flag leaf characteristic as illustrated in FIG. 7, to obtain a plant designated d28267 which was selfed to the $F_3$ generation. The resulting $F_2$ plants were found to be segregating for genetic male sterility with reverse drooping flag leaves (msmsdd) and male fertility with erect flag leaves (MsmsDd). A female fertile genetically male sterile $F_3$ plant having a reverse drooping flag leaf and standard uppermost internode length (msmsddEuiEui) was crossed to the fully fertile IR50-eui variety having an erect flag leaf and an elongated uppermost internode (MsMsDDeuieui). The resulting $F_1$ plant (MsmsDdEuieui) was selfed to the $F_2$ generation and plants were selected for (1) genetic male sterility, the perennial trait, a reverse drooping flag leaf as illustrated in FIG. 7, and an elongated uppermost internode length (msmsddeuieui) designated GPAL or 9005-8717A, and for (2) full fertility, the perennial trait, an erect flag leaf, and elongated peduncle (MsmsDdeuieui) designated GPBL or 9005-8717B. It should be recognized that the euieui genes are expressed to a greater degree on male fertile plants since the expression of this gene has been found to be closely linked to the male fertility factor. These genotypes were verified in the $F_3$ generations and are capable of biparental mating wherein GPBL or 9005-8717B serves as a maintainer for GPAL or 9005-8717A. Such GPAL plants possess fully exserted stigmas, flag leaves which possess the reverse drooping configuration of FIG. 7, and the ability to form rice grains which possess straw-colored hulls which can serve as a dominantly inherited genetic marker.

Seeds capable of forming the perennial female fertile genetically male sterile *Oryza sativa* plants designated 9005-8717A and the perennial female fertile male fertile maintainer plants for the same designated 9005-8717B are to be deposited as a binary seed blend under the Budapest Treaty in the American Type Culture collection under Accession No. 40920. These seed deposits will be made available upon the maturation of this application into a patent. However, the availability of these seeds is not to be construed as a license to practice the invention in contravention of the rights granted under the authority of any government in accordance with its patent or breeder's rights law.

Such 9005-8717A seeds can be used when carrying out the process of the present invention as described herein in conjunction with FIGS. 18 and 19. Preferred publicly available restorers for use with these perennial female fertile genetically male sterile *Oryza sativa* plants are IR24, IR26, IR50, 97B and D297B which are available in the Philippines, the Peoples Republic of China and in the United States. Most indica restorer lines and most United States rice varieties could be similarly selected. Varieties such as Bluebelle, Dawn, and Pecos possess gold-colored hulls which can serve as a recessively inherited genetic marker. Additional parent plants which satisfy the prerequisites set forth herein can be independently provided with equally advantageous results.

Although the invention has been described with preferred embodiments, it is to be understood that variations and modifications may be resorted to as will be apparent to those skilled in the art. Such variations and modifications are to be considered within the purview and scope of the claims appended hereto.

We claim:

1. An *Oryza sativa* seed product consisting essentially of seeds which upon growth yield perennial female fertile cytoplasmically male sterile rice plants having exserted stigmas, flag leaves which in the absence of cutting generally extend upwardly to a lesser maximum height than the tips of the panicles whereby said panicles are well disposed to receive pollen from nearby plants and the disposition of said flag leaves below the tips of the panicles is attributable to recessive genes, and the ability to form seeds which exhibit a visible dominantly inherited genetic marker on or about the rice hull.

2. An *Oryza sativa* seed product according to claim 1 wherein said perennial female fertile cytoplasmically male sterile rice plants have panicles which are exserted in the absence of the application of a growth hormone.

3. An *Oryza sativa* seed product according to claim 2 wherein said seeds upon growth yield perennial female fertile cytoplasmically male sterile rice plants having flag leaves which possess a reverse drooping configuration.

4. A binary *Oryza sativa* seed product consisting of seeds which upon growth yield from the first of said two components perennial female fertile male sterile rice plants (1) wherein said male sterility is attributable solely to nuclear genes and said plants having exserted stigmas, flag leaves which in the absence of cutting generally extend upwardly to a lesser maximum height than the tips of the panicles whereby said panicles are well disposed to receive pollen from nearby plants and the disposition of said flag leaves below the tips of said panicles is attributable to recessive genes, and the ability to form seeds which exhibit a visible dominantly inherited genetic marker on or about the rice hull, and yield from the second of said two components perennial maintainer plants (2) for said (1) plants.

5. A binary *Oryza sativa* seed product according to claim 4 wherein said plants (1) possess reverse drooping flag leaves which are attributable to recessive genes.

6. Plants of *Oryza sativa* which exhibit a perennial growth habit, male sterility, exserted stigmas, flag leaves which in the absence of cutting generally extend upwardly to a lesser maximum height than the tips of the panicles whereby said panicles are well disposed to receive pollen from nearby plants and the disposition of said flag leaves below the tips of said panicles is attributable to recessive genes, and the ability to form seeds which exhibit a visible dominantly inherited genetic marker on or about the rice hull.

7. Plants of *Oryza sativa* according to claim 6 which exhibit panicles which are exserted in the absence of the application of a growth hormone.

8. Plants of i Oryza sativa according to claim 6 wherein said male sterility is cytoplasmic in character.

9. Plants of *Oryza sativa* according to claim 8 wherein said flag leaves exhibit a reverse drooping configuration which is attributable to recessive genes.

10. Plants of *Oryza sativa* according to claim 6 wherein said male sterility is attributable solely to nuclear genes.

11. Plants of *Oryza sativa* according to claim 10 wherein said flag leaves exhibit a reverse drooping configuration which is attributable to recessive genes.

* * * * *